US012723010B2

(12) United States Patent
Cho et al.

(10) Patent No.: US 12,723,010 B2
(45) Date of Patent: Sep. 1, 2026

(54) ETHYLENE OLIGOMERIZATION METHOD, AND ETHYLENE OLIGOMER THEREOF

(71) Applicant: HANWHA TOTALENERGIES PETROCHEMICAL CO., LTD., Seosan-si (KR)

(72) Inventors: Kye Sung Cho, Seosan-si (KR); Dong Geun Lee, Seosan-si (KR); Sang Joon Oh, Seosan-si (KR); Ho Sik Chang, Seosan-si (KR); Jin Suk Lee, Seosan-si (KR)

(73) Assignee: HANWHA TOTALENERGIES PETROCHEMICAL CO., LTD., Seosan-si (KR)

( * ) Notice: Subject to any disclaimer, the term of this patent is extended or adjusted under 35 U.S.C. 154(b) by 198 days.

(21) Appl. No.: 18/713,754

(22) PCT Filed: Sep. 23, 2022

(86) PCT No.: PCT/KR2022/014243
§ 371 (c)(1),
(2) Date: May 28, 2024

(87) PCT Pub. No.: WO2023/177031
PCT Pub. Date: Sep. 21, 2023

(65) Prior Publication Data

US 2025/0109082 A1 Apr. 3, 2025

(30) Foreign Application Priority Data

Mar. 15, 2022 (KR) ........................ 10-2022-0032352

(51) Int. Cl.
*C07C 2/34* (2006.01)

(52) U.S. Cl.
CPC ............ *C07C 2/34* (2013.01); *C07C 2531/14* (2013.01); *C07C 2531/22* (2013.01)

(58) Field of Classification Search
CPC ... C07C 2/34; C07C 2531/14; C07C 2531/22; C07C 2531/12; C07C 2/88;
(Continued)

(56) References Cited

U.S. PATENT DOCUMENTS 7,511,183 B2 3/2009 Blann et al.
8,859,696 B2 * 10/2014 Hanton .................... C07C 2/36 526/133
(Continued)

FOREIGN PATENT DOCUMENTS

KR 1020150006474 A 1/2015
KR 101641545 B1 7/2016
(Continued)

OTHER PUBLICATIONS

Hanton et al., “Bis(imino)pyridine Complexes of the First-Row Transition Metals: Alternative Methods of Activation”, Organometallics, vol. 27, No. 21, 2008, pp. 5712-5716.
(Continued)

*Primary Examiner* — Ellen M McAvoy
(74) *Attorney, Agent, or Firm* — Harness, Dickey & Pierce, P.L.C.

(57) ABSTRACT

The present invention provides: an ethylene oligomerization method in which an ethylene oligomer is produced by reacting a chromium complex, an organic aluminium compound, and an organic zinc compound with ethylene; and the ethylene oligomer thereof.

20 Claims, 2 Drawing Sheets

(58) Field of Classification Search
CPC ... C07C 2531/24; C07C 11/02; C07C 11/107; C07C 2527/188; Y02P 20/52
See application file for complete search history.

(56) References Cited

U.S. PATENT DOCUMENTS

| | | | | |
|---|---|---|---|---|
| 9,447,202 | B2 * | 9/2016 | Hanton | C08F 4/30 |
| 11,052,384 | B2 | 7/2021 | Lee et al. | |
| 11,148,127 | B2 | 10/2021 | Lee et al. | |
| 2011/0282016 | A1 | 11/2011 | Carter et al. | |
| 2019/0308179 | A1 * | 10/2019 | Lee | B01J 31/189 |
| 2021/0229084 | A1 * | 7/2021 | Lee | B01J 31/1608 |
| 2023/0100188 | A1 * | 3/2023 | Jung | B01J 31/188 585/513 |
| 2023/0331753 | A1 * | 10/2023 | Kim | B01J 31/188 |
| 2025/0100953 | A1 * | 3/2025 | Kim | C07F 9/46 |
| 2025/0188003 | A1 * | 6/2025 | Cho | B01J 37/04 |

FOREIGN PATENT DOCUMENTS

| | | | |
|---|---|---|---|
| KR | 101766224 | B1 | 8/2017 |
| KR | 1020200129723 | A | 11/2020 |

OTHER PUBLICATIONS

International Search Report (English and Korean) and Written Opinion of the ISA (Korean) issued in PCT/KR2022/014243, mailed Jan. 2, 2023; ISA/KR.

* cited by examiner

ETHYLENE OLIGOMERIZATION METHOD, AND ETHYLENE OLIGOMER THEREOF

CROSS-REFERENCE TO RELATED APPLICATIONS

This application is a U.S. National Phase application under 35 U.S.C. 371 of International Application No. PCT/KR2022/014243, filed on Sep. 23, 2022, which claims the benefit of Korean Patent Application No. 10-2022-0032352, filed on Mar. 15, 2022. The entire disclosures of the above applications are incorporated herein by reference.

FIELD

The present disclosure relates to a method for oligomerization of ethylene and an ethylene oligomer produced thereby.

BACKGROUND

Among ethylene oligomers, 1-hexene and 1-octene are materials that are used in large amounts as comonomers in the production of polyolefins such as polyethylene, and the demand therefor is steadily increasing as the production of polyolefins using homogeneous metallocene-based catalysts increases.

In a conventional art, 1-hexene and/or 1-octene could be obtained by oligomerizing ethylene in the Shell Higher Olefin Process (SHOP) based on a nickel catalyst to produce various 1-alkenes having about 4 to about 30 carbon atoms, and separating 1-hexene and/or 1-octene from the 1-alkenes.

Since then, a catalyst system was developed that could produce 1-hexene or 1-octene in high yield by increasing selectivity to 1-hexene or 1-octene in the ethylene oligomerization reaction.

As a representative example, U.S. Pat. No. 7,511,183B2 discloses a method of preparing a catalyst, which is capable of selectively producing 1-octene and 1-hexene, using a trivalent chromium compound ($CrCl_3$ or $Cr(acac)_3$), a bisphosphine ligand ($iPrN(PPh_2)_2$), and methylaluminoxane (MAO).

However, the catalyst system was reported to have problems that not only require the use of expensive MAO in large amounts (Al/Cr=300-500) to achieve a commercially usable level of activity, but also produce a large amount of polyethylene (PE) that seriously impair process stability (Organometallics, 27, 5712-5716).

In addition, at high temperatures, the catalyst activity of the oligomerization catalyst system decreases, resulting in reduction in the production of and selectivity to olefins, especially 1-octene, and resulting in increased production of by-products, which causes tube clogging and fouling. This inevitably leads to process shutdown, causing serious problems in the olefin polymerization process.

Specifically, polyethylene produced as a by-product forms a polymer layer, and a polymer layer is formed again on the formed polymer layer, lowering the fluid flow rate, and the polymer coating layer formed along the reactor wall acts as an insulating material that negatively affects heat transfer. In other words, tube clogging and fouling occur, and thus secondary processing to remove the polymer layer is required, leading to frequent process shutdowns.

Therefore, there is a need for an improved method for oligomerization of ethylene that may not only produce 1-hexene and 1-octene with high selectivity without reducing catalyst activity, but also significantly reduce the production of polyethylene that impairs process stability.

SUMMARY

Technical Problem

The present disclosure provides a method for oligomerization of ethylene that may not only produce 1-hexene and 1-octene with high selectivity without reducing catalyst activity, but also significantly reduce the production of polyethylene that impairs process stability, and an ethylene oligomer produced thereby.

Technical Solution

The present disclosure provides a method for oligomerization of ethylene method that suppresses the production of polyethylene while maintaining enhanced catalyst activity, and increases selectivity to especially 1-octene, and an ethylene oligomer produced thereby.

Specifically, the present disclosure provides a method for oligomerization of ethylene, including a step of producing an ethylene oligomer by reacting ethylene with a catalyst, which contains a transition metal compound and a heteroatom ligand represented by the formula (R)nPNP(R)m (wherein R's are the same as or different from each other and are each independently selected from among any homo- and hetero-hydrocarbyl groups, and n and m are integers greater than 1), a cocatalyst, and a chain transfer agent in the presence of an organic compound.

Hereinafter, the present disclosure will be described by way of an example where the catalyst may be a chromium complex, the cocatalyst may be an organoaluminum compound, an organoboron compound, or the like, and the chain transfer agent is an organozinc compound.

For example, the present disclosure provides a method for oligomerization of ethylene of producing an ethylene oligomer by reacting ethylene with a chromium complex, an organoaluminum compound, and an organozinc compound, and an ethylene oligomer produced thereby.

The present disclosure provides a method for oligomerization of ethylene, including a step of producing an ethylene oligomer by reacting ethylene with a chromium complex represented by Formula 1 below, an organoaluminum compound represented by Formula 2 below, and a compound represented by Formula 3 below at a temperature lower than 60° C. in the presence of an organic solvent.

[Formula 1]

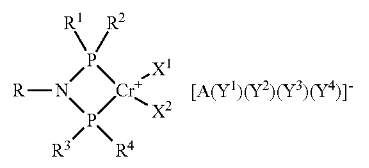

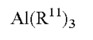

[Formula 2]

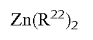

[Formula 3]

In Formulas 1 to 3 above,

R may be $C_1$-$C_{60}$ alkyl, $C_6$-$C_{60}$ aryl, or $C_2$-$C_{60}$ heteroaryl containing at least one heteroatom selected from the group consisting of O, N, S, Si and P; $R^1$ to $R^4$ may be each independently $C_1$-$C_{60}$ alkyl, $C_6$-$C_{60}$ aryl, or $C_2$-$C_{60}$ heteroaryl containing at least one heteroatom selected from the group consisting of O, N, S, Si and P; $X^1$ and $X^2$ may be each independently halogen, $C_1$-$C_{30}$ alkyl, $C_1$-$C_{30}$ alkylcarboxylate, acetylacetonate, or $C_1$-$C_{30}$ hydrocarbyl containing at least one selected from among ether and amino; A may be boron or aluminum; $Y^1$ to $Y^4$ may be each independently fluorine-substituted $C_6$-$C_{60}$ aryl, fluorine-substituted $C_6$-$C_{60}$ heteroaryl containing at least one heteroatom selected from the group consisting of O, N, S, Si and P, fluorine-substituted $C_6$-$C_{60}$ aryloxy, or fluorine-substituted $C_6$-$C_{60}$ alkoxy; $R^{11}$ may be $C_4$-$C_8$ alkyl; and $R^{22}$ may be $C_1$-$C_8$ alkyl.

Here, the alkyl, aryl or heteroaryl in R, $R^1$ to $R^4$, $X^1$, $X^2$, $Y^1$ to $Y^4$, $R^{11}$, and $R^{22}$ may be further substituted with at least one selected from among $C_1$-$C_{30}$ alkyl, $C_6$-$C_{30}$ aryl, $C_1$-$C_{30}$ alkoxy, mono($C_1$-$C_{30}$)alkylamino, di($C_1$-$C_{30}$)alkylamino, tri($C_1$-$C_{30}$)alkylamino, mono($C_6$-$C_{30}$)arylamino, di($C_6$-$C_{30}$)arylamino, tri($C_6$-$C_{30}$)arylamino, mono($C_1$-$C_{30}$) alkylsilyl, di($C_1$-$C_{30}$)alkylsilyl, tri($C_1$-$C_{30}$)alkylsilyl, mono ($C_6$-$C_{30}$)arylsilyl, di($C_6$-$C_{30}$)arylsilyl, and tri($C_6$-$C_{30}$)arylsilyl.

The present disclosure also provides an ethylene oligomer produced by reacting ethylene with the chromium complex represented by Formula 1 and the organoaluminum compound represented by Formula 2.

Advantageous Effects

The method for oligomerization of ethylene according to one embodiment of the present disclosure may not only produce 1-hexene and 1-octene with high selectivity without reducing catalyst activity, but also significantly reduce the production of polyethylene that impairs process stability,

DETAILED DESCRIPTION

Figure 1:
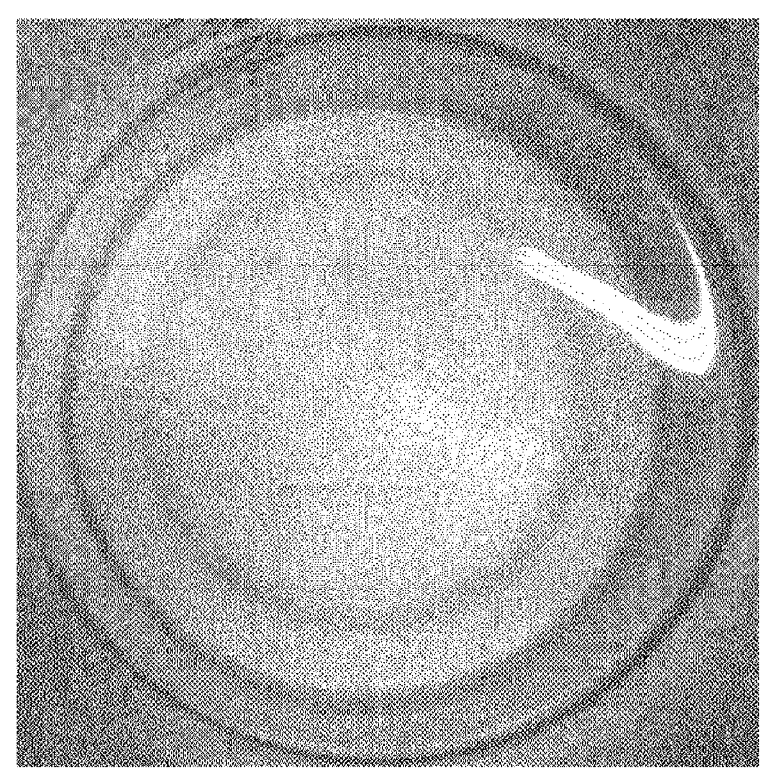
FIG. 1 is a photograph of the polymer produced after the reaction in Example 1 of the present disclosure.

Hereinafter, some embodiments of the present disclosure will be described in detail with reference to the accompanying illustrative drawings. In the drawings, like reference numerals are used to denote like elements throughout the drawings, even if they are shown on different drawings. Further, in the following description of embodiments of the present disclosure, detailed description of related known configurations or functions will be omitted when it may obscure the subject matter of the present disclosure. When the expression "include", "have", "comprise", or the like as mentioned herein is used, any other part may be added unless the expression "only" is used. When an element is expressed in the singular form, the element may cover the plural form unless a special mention is explicitly made of the element.

In addition, terms, such as first, second, A, B, (a), (b) or the like may be used herein to describe components of the present disclosure. Each of these terms is not used to define essence, order, sequence, or number of components but is used merely to distinguish the corresponding component from other component(s).

In describing the positional relationship between components, if two or more components are described as being "connected", "combined", or "coupled" to each other, it should be understood that two or more components may be directly "connected", "combined", or "coupled" to each other, and that two or more components may be "connected", "combined", or "coupled" to each other with another component "interposed" therebetween. In this case, another component may be included in at least one of the two or more components that are "connected", "combined", or "coupled" to each other.

In the description of temporal relationships related to components, operating methods, production methods, or the like, time relative terms, such as "after", "subsequent to", "next", "before", or the like, used herein to describe a temporal relationship between events, operations, or the like may include events or cases that do not occur consecutively unless terms, such as "directly" or "immediately", are used.

Meanwhile, numerical values for components or information corresponding thereto (e.g., levels, etc.), which are mentioned herein, may be interpreted as including an error range caused by various factors (e.g., process factors, internal or external impacts, noise, etc.) even if an explicit description thereof is not provided.

As used herein, the term "alkyl", when the number of carbon atoms is not particularly limited, refers to a saturated straight or branched non-cyclic hydrocarbon having 1 to 60 carbon atoms, preferably 1 to 30 carbon atoms, preferably 1 to 20 carbon atoms in one embodiment, preferably 1 to 10 carbon atoms in one embodiment, preferably 1 to 7 carbon atoms in one embodiment. The term "lower alkyl" refers to a straight or branched alkyl having 1 to 7 carbon atoms, preferably 1 to 5 carbon atoms in one embodiment. Representative saturated straight alkyls include -methyl, -ethyl, -n-propyl, -n-butyl, -n-pentyl, -n-hexyl, -n-heptyl, -n-octyl, -n-nonyl and -n-decyl, whereas saturated branched alkyls include -isopropyl, -sec-butyl, -isobutyl, -tert-butyl, isopentyl, 2-methylhexyl, 3-methylbutyl, 2-methylpentyl, 3-methylpentyl, 4-methylpentyl, 2-methylhexyl, 3-methylhexyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, and 3,3-diethylhexyl.

In the present specification, "$C_1$-$C_{10}$" means 1 to 10 carbon atoms. For example, $C_1$-$C_{10}$ alkyl means an alkyl having 1 to 10 carbon atoms.

As used herein, the terms "halogen" and "halo" refer to fluorine, chlorine, bromine, or iodine.

As used herein, the term "fluorine-substituted aryl", "fluorine-substituted aryloxy", and "fluorine-substituted alkoxy" respectively refer to aryl, aryloxy, and alkoxy groups in which at least one hydrogen atom is substituted with a fluorine atom. For example, haloaryls include $-C_6H_4F$, $-C_6H_3F_2$, $-C_6HF_4$, and the like. Here, aryl and halogen are as defined above, and alkoxy is as defined below.

As used herein, the term "alkoxy" refers to —O-(alkyl), including $-OCH_3$, $-OCH_2CH_3$, $-O(CH_2)_2CH_3$, $-O(CH_2)_3CH_3$, $-O(CH_2)_4CH_3$, $-O(CH_2)_5CH_3$, and the like, wherein the alkyl is as defined above.

As used herein, the term "lower alkoxy" refers to —O-(lower alkyl), wherein the lower alkyl is as defined above.

As used herein, the term "aryl" refers to a carbocyclic aromatic group containing 5 to 10 cyclic atoms. Representative examples include phenyl, tolyl, xylyl, naphthyl, tetrahydronaphthyl, anthracenyl, fluorenyl, indenyl, azulenyl, and the like, without being limited thereto. The carbocyclic aromatic group may be optionally substituted.

The term "aryloxy" refers to RO—, wherein R is the aryl defined above. The term "arylthio" is RS—, wherein R is the aryl defined above.

As used herein, the term "mono-alkylamino" refers to —NH(alkyl), including $—NHCH_3$, $—NHCH_2CH_3$, $—NH(CH_2)_2CH_3$, $—NH(CH_2)_3CH_3$, $—NH(CH_2)_4CH_3$, $—NH(CH_2)_5CH_3$, and the like, wherein the alkyl is as defined above.

As used herein, the term "di-alkylamino" refers to N(alkyl)(alkyl), including $—N(CH_3)_2$, $—N(CH_2CH_3)_2$, $—N((CH_2)_2CH_3)_2$, $—N(CH_3)(CH_2CH_3)$, and the like, wherein each alkyl is the alkyl defined above.

As used herein, the term "mono-alkylsilyl" refers to $—SiH_2$(alkyl), including $—SiH_2CH_3$, $—SiH_2CH_3$, $—SiH_2(CH_2)_2CH_3$, $—SiH_2(CH_2)_3CH_3$, $—SiH_2(CH_2)_4CH_3$, $—SiH_2(CH_2)_5CH_3$, and the like, wherein the alkyl is as defined above.

As used herein, the term "di-alkylsilyl" refers to —SiH(alkyl)(alkyl), including $—SiH(CH_3)_2$, $—SiH(CH(CH_3)_2)(CH_3)$, $—SiH((CH_2)_2CH_3)_2$, $—SiH(CH_3)(CH_2CH_3)$, and the like, wherein each alkyl is as defined above.

As used herein, the term "trialkylsilyl" refers to Si(alkyl)(alkyl)(alkyl), including $—Si(CH_3)_3$, $—Si(CH_2(CH_3))_3$, $—Si((CH_2)_2CH_3)_3$, $—Si(CH_3)_2(CH_2CH_3)$, and the like, wherein each alkyl is as defined above.

As used herein, the terms "monoarylsilyl", "diarylsilyl", and "triarylsilyl" refer to substituents having aryl instead of alkyl in "monoalkylsilyl", "dialkylsilyl", or "trialkylsilyl".

As used herein, the term "heteroatom", unless otherwise specified, refers to N, O, S, P or Si, without being thereto.

Hereinafter, the method for oligomerization of ethylene according to an embodiment of the present disclosure will be described in detail.

The present disclosure provides a method for oligomerization of ethylene, including a step of producing an ethylene oligomer by reacting ethylene with a catalyst, which contains a transition metal compound and a heteroatom ligand represented by the formula (R)nPNP(R)m (wherein R's are the same as or different from each other and are each independently selected from among any homo- and hetero-hydrocarbyl groups, and n and m are integers greater than 1), a cocatalyst, and a chain transfer agent in the presence of an organic compound.

Hereinafter, the present disclosure will be described by way of an example where the catalyst may be a chromium complex, the cocatalyst may be an organoaluminum compound, an organoboron compound, or the like, and the chain transfer agent is an organozinc compound.

For example, the present disclosure provides a method for oligomerization of ethylene, including a step of producing an ethylene oligomer by reacting ethylene with a chromium complex represented by Formula 1 below, an organoaluminum compound represented by Formula 2 below, and a compound represented by Formula 3 below at, for example, lower than 60° C., in the presence of an organic solvent.

[Formula 1]

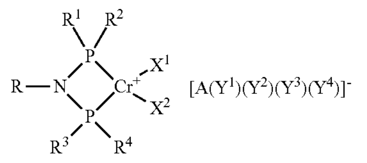

$Al(R^{11})_3$ [Formula 2]

$Zn(R^{22})_2$ [Formula 3]

In Formulas 1 to 3 above,

R may be $C_1$-$C_{60}$ alkyl, $C_6$-$C_{60}$ aryl, or $C_2$-$C_{60}$ heteroaryl containing at least one heteroatom selected from the group consisting of O, N, S, Si and P;

$R^1$ to $R^4$ may be each independently $C_1$-$C_{60}$ alkyl, $C_6$-$C_{60}$ aryl, or $C_2$-$C_{60}$ heteroaryl containing at least one heteroatom selected from the group consisting of O, N, S, Si and P;

$X^1$ and $X^2$ may be each independently halogen, $C_1$-$C_{30}$ alkyl, $C_1$-$C_{30}$ alkylcarboxylate, acetylacetonate, or $C_1$-$C_{30}$ hydrocarbyl containing at least one selected from among ether and amino;

A may be boron or aluminum;

$Y^1$ to $Y^4$ may be each independently fluorine-substituted $C_6$-$C_{60}$ aryl, fluorine-substituted $C_6$-$C_{60}$ heteroaryl containing at least one heteroatom selected from the group consisting of O, N, S, Si and P, fluorine-substituted $C_6$-$C_{60}$ aryloxy, or fluorine-substituted $C_6$-$C_{60}$ alkoxy;

$R^{11}$ may be $C_4$-$C_8$ alkyl; and $R^{22}$ may be $C_1$-$C_8$ alkyl.

Here, the alkyl, aryl or heteroaryl in R, $R^1$ to $R^4$, $X^1$, $X^2$, $Y^1$ to $Y^4$, $R^{11}$, and $R^{22}$ may be further substituted with at least one selected from among $C_1$-$C_{30}$ alkyl, $C_6$-$C_{30}$ aryl, $C_1$-$C_{30}$ alkoxy, mono($C_1$-$C_{30}$)alkylamino, di($C_1$-$C_{30}$)alkylamino, tri($C_1$-$C_{30}$)alkylamino, mono($C_6$-$C_{30}$)arylamino, di($C_6$-$C_{30}$)arylamino, tri($C_6$-$C_{30}$)arylamino, mono($C_1$-$C_{30}$)alkylsilyl, di($C_1$-$C_{30}$)alkylsilyl, tri($C_1$-$C_{30}$)alkylsilyl, mono($C_6$-$C_{30}$)arylsilyl, di($C_6$-$C_{30}$)arylsilyl, and tri($C_6$-$C_{30}$)arylsilyl.

The method for oligomerization of ethylene according to the present disclosure is capable of producing an ethylene oligomer with high selectivity and conversion even at low temperatures by using the chromium complex represented by Formula 1 and the organoaluminum compound represented by Formula 2, which exhibit excellent catalytic activity.

In addition, the method for oligomerization of ethylene according to the present disclosure is capable of oligomerizing ethylene by using the specific chromium complex represented by Formula 1, which exhibits high catalytic activity, even without using conventional expensive methylaluminoxane.

Preferably, the step of producing an ethylene oligomer according to an embodiment of the present disclosure may include an organozinc compound. By introducing the organozinc compound in the step of producing an ethylene oligomer according to an embodiment of the present disclosure, it is possible to maintain process stability by dramatically suppressing the production of by-products such as polyolefins while maintaining catalytic activity.

Preferably, the method for oligomerization of ethylene according to an embodiment of the present disclosure may include steps of: reacting the chromium complex represented by Formula 1 with the organoaluminum compound represented by Formula 2 in the presence of an organic solvent; and sequentially adding the organozinc compound represented by Formula 3 and ethylene to the mixture of the above step. By adding the organozinc compound represented by Formula 3 and ethylene after the step of reacting the chromium complex represented by Formula 1 with the organoaluminum compound represented by Formula 2, it is possible to dramatically reduce the production of reaction by-products such as polyethylene while increasing catalyst activity.

The ethylene oligomerization reaction according to one embodiment of the present disclosure may be performed at higher than 30° C. to lower than 60° C., preferably higher than 30° C. to lower than 50° C., and the reaction time may be 10 minutes to 2 hours, preferably 10 minutes to 1 hour.

The method for oligomerization of ethylene according to one embodiment of the present disclosure may be performed in any reactor, but is preferably performed in a continuous stirred tank reactor (CSTR) or a plug-flow reactor (PFR), more preferably a continuous stirred tank reactor (CSTR).

When the reactor according to one embodiment of the present disclosure is a continuous stirred tank reactor, it is preferred that 80% or less, preferably 50% or less, of the total volume of the reactor is maintained in a liquid state.

According to one embodiment of the present disclosure, the molar ratio between the chromium complex and the organoaluminum compound represented by Formula 2 may be 1:10 to 500, preferably 1:100 to 300, more preferably 1:150 to 250.

According to one embodiment of the present disclosure, the molar ratio between the chromium complex and the organozinc compound represented by Formula 3 may be 1:100 to 1,200, preferably 1:200 to 800, more preferably 1:300 to 700.

In a more preferred combination of the specific chromium complex represented by Formula 1 and the compound represented by Formula 2, which are used in the method for oligomerization of ethylene according to the present disclosure, in Formula 1 and Formula 2 of the present disclosure, R may be $C_1$-$C_{60}$ alkyl; $R^1$ to $R^4$ may be each independently $C_6$-$C_{60}$ aryl; $X^1$ and $X^2$ may be each independently halogen, $C_1$-$C_{30}$ alkyl, $C_1$-$C_{30}$ alkylcarboxylate, acetylacetonate, or $C_1$-$C_{30}$ hydrocarbyl containing ether; A may be boron or aluminum; $Y^1$ to $Y^4$ may be each independently fluorine-substituted $C_6$-$C_{60}$ aryl, fluorine-substituted $C_6$-$C_{60}$ aryloxy, or fluorine-substituted $C_6$-$C_{60}$ alkoxy; and $R^{11}$ to $R^{13}$ may be each independently $C_1$-$C_{20}$ alkyl, wherein the alkyl in R and the aryl in $R^1$ to $R^4$ may be further substituted with at least one selected from among $C_1$-$C_{30}$ alkyl, $C_6$-$C_{30}$ aryl, $C_1$-$C_{30}$ alkoxy, mono($C_1$-$C_{30}$)alkylamino, di($C_1$-$C_{30}$)alkylamino, tri($C_1$-$C_{30}$)alkylamino, mono($C_6$-$C_{30}$)arylamino, di($C_6$-$C_{30}$)arylamino, tri($C_6$-$C_{30}$)arylamino, monoalkylsilyl, di($C_1$-$C_{30}$)alkylsilyl, tri($C_1$-$C_{30}$)alkylsilyl, mono($C_6$-$C_{30}$)arylsilyl, di($C_6$-$C_{30}$)arylsilyl, and tri($C_6$-$C_{30}$)arylsilyl.

In a more preferred combination of Formula 1 and Formula 2 according to one embodiment of the present disclosure, in Formula 1 and Formula 2, R may be $C_1$-$C_{30}$ alkyl; $R^1$ to $R^4$ may be each independently $C_6$-$C_{60}$ aryl; $X^1$ and $X^2$ may be each independently halogen, $C_1$-$C_{30}$ alkyl, $C_1$-$C_{30}$ alkylcarboxylate, acetylacetonate, or $C_1$-$C_{20}$ hydrocarbyl containing ether; A may be boron; $Y^1$ to $Y^4$ may be each independently fluorine-substituted $C_6$-$C_{30}$ aryl, fluorine-substituted $C_6$-$C_{30}$ aryloxy, or fluorine-substituted $C_6$-$C_{30}$ alkoxy; and $R^{11}$ to $R^{13}$ may be each independently $C_1$-$C_{20}$ alkyl, wherein the alkyl in R and the aryl in $R^1$ to $R^4$ may be further substituted with at least one selected from among $C_1$-$C_{20}$ alkyl, $C_6$-$C_{20}$ aryl, $C_1$-$C_{20}$ alkoxy, mono($C_1$-$C_{20}$)alkylamino, di($C_1$-$C_{20}$)alkylamino, tri($C_1$-$C_{20}$)alkylamino, mono($C_6$-$C_{20}$)arylamino, di($C_6$-$C_{20}$)arylamino, tri($C_6$-$C_{20}$)arylamino, mono($C_1$-$C_{20}$)alkylsilyl, di($C_1$-$C_{20}$)alkylsilyl, tri($C_1$-$C_{20}$)alkylsilyl, mono($C_6$-$C_{20}$)arylsilyl, di($C_6$-$C_{20}$)arylsilyl, and tri($C_6$-$C_{20}$)arylsilyl.

More preferably, R may be $C_1$-$C_{20}$ alkyl; $R^1$ to $R^4$ may be each independently $C_6$-$C_{20}$ aryl; $X^1$ and $X^2$ may be each independently halogen, $C_1$-$C_{20}$ alkyl, $C_1$-$C_{20}$ alkylcarboxylate, or acetylacetonate; A may be boron; $Y^1$ to $Y^4$ may be each independently fluorine-substituted $C_6$-$C_{20}$ aryl, fluorine-substituted $C_6$-$C_{20}$ aryloxy, or fluorine-substituted $C_6$-$C_{20}$ alkoxy; and $R^{11}$ to $R^{13}$ may be each independently $C_1$-$C_{10}$ alkyl, wherein the alkyl in R and the aryl in $R^1$ to $R^4$ may be further substituted with at least one selected from among $C_1$-$C_{10}$ alkyl, $C_6$-$C_{12}$ aryl, $C_1$-$C_{10}$ alkoxy, mono($C_1$-$C_{10}$)alkylamino, di($C_6$-$C_{12}$)alkylamino, tri($C_1$-$C_{10}$)alkylamino, mono($C_6$-$C_{12}$)arylamino, di($C_6$-$C_{12}$)arylamino, tri($C_6$-$C_{12}$)arylamino, mono($C_1$-$C_{10}$)alkylsilyl, di($C_1$-$C_{10}$)alkylsilyl, and tri($C_1$-$C_{10}$)alkylsilyl. More preferably, R may be $C_1$-$C_{10}$ alkyl; $R^1$ to $R^4$ may be each independently $C_6$-$C_{12}$ aryl; $X^1$ and $X^2$ may be each independently halogen; A may be boron; $Y^1$ to $Y^4$ may be each independently fluorine-substituted $C_6$-$C_{12}$ aryl; and $R^{11}$ to $R^{13}$ may be each independently $C_1$-$C_7$ alkyl, wherein the alkyl in R and the aryl in $R^1$ to $R^4$ may be further substituted with at least one selected from among $C_1$-$C_7$ alkyl, and tri($C_1$-$C_7$)alkylsilyl.

In terms of catalytic efficiency, selectivity to an ethylene oligomer, and inhibition of the production of polyolefins, Formula 1 may more preferably be represented by Formula 4 below:

[Formula 4]

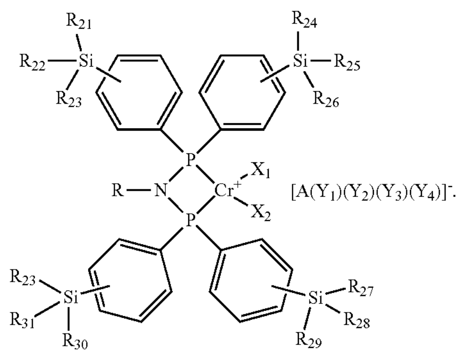

In Formula 4 above,

R may be $C_1$-$C_{30}$ alkyl, or $C_6$-$C_{60}$ aryl;

$X^1$ and $X^2$ may be each independently halogen, $C_1$-$C_{20}$ alkyl, $C_1$-$C_{20}$ alkylcarboxylate, acetylacetonate, or $C_1$-$C_{20}$ hydrocarbyl containing ether;

A may be boron or aluminum;

$Y^1$ to $Y^4$ may be each independently fluorine-substituted $C_6$-$C_{60}$ aryl, fluorine-substituted $C_6$-$C_{30}$ aryloxy, or fluorine-substituted $C_6$-$C_{30}$ alkoxy; and $R^{21}$ to $R^{32}$ may be each independently $C_1$-$C_{20}$ alkyl, wherein the alkyl or aryl in R may be further substituted with at least one selected from among $C_1$-$C_{20}$ alkyl, $C_6$-$C_{20}$ aryl, $C_1$-$C_{20}$ alkoxy, mono($C_1$-$C_{20}$)alkylamino, di($C_1$-$C_{20}$)alkylamino, tri($C_1$-$C_{20}$)alkylamino, mono($C_1$-$C_{20}$)arylamino, di($C_6$-$C_{20}$)arylamino, and tri($C_6$-$C_{20}$)arylamino.

The chromium complex represented by Formula 4 according to one embodiment of the present disclosure has improved catalytic activity and improved selectivity to an ethylene oligomer as a trialkylsilyl group, which is a specific substituent, is introduced to phenyl (Ph) bonded to phosphorus (P).

Preferably, in Formula 4 according to one embodiment of the present disclosure, R may be $C_1$-$C_{20}$ alkyl; $X^1$ and $X^2$ may be each independently halogen, $C_1$-$C_{20}$ alkyl, $C_1$-$C_{20}$ alkylcarboxylate, or acetylacetonate; A may be boron; and $Y^1$ to $Y^4$ may be each independently fluorine-substituted $C_6$-$C_{20}$ aryl, or fluorine-substituted $C_6$-$C_{20}$ aryloxy, and preferably, R may be $C_1$-$C_{10}$ alkyl; $X^1$ and $X^2$ may be each independently halogen or $C_1$-$C_{10}$ alkyl; A may be boron; and $Y^1$ to $Y^4$ may be each independently fluorine-substituted $C_6$-$C_{12}$ aryl.

More preferably, in Formula 4 according to one embodiment of the present disclosure, R may be $C_1$-$C_5$ alkyl; $X^1$ and $X^2$ may be chlorine; A may be boron; and $Y^1$ to $Y^4$ may be $(C_6F_5)_4$; and $R^{21}$ to $R^{32}$ may be each independently $C_5$-$C_8$ alkyl.

Preferably, Formula 4 according to one embodiment of the present disclosure may be represented by Formula 5 below:

[Formula 5]

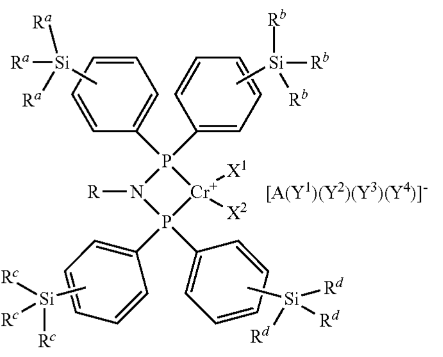

In Formula 5 above,

R may be $C_1$-$C_{20}$ alkyl, or $C_6$-$C_{20}$ aryl;

$X^1$ and $X^2$ may be each independently halogen, $C_1$-$C_{20}$ alkyl, $C_1$-$C_{20}$ alkylcarboxylate, acetylacetonate, or $C_1$-$C_{20}$ hydrocarbyl containing ether;

A may be boron or aluminum;

$Y^1$ to $Y^4$ may be each independently fluorine-substituted $C_6$-$C_{20}$ aryl, fluorine-substituted $C_6$-$C_{20}$ aryloxy, or fluorine-substituted $C_6$-$C_{20}$ alkoxy; and $R^a$ to $R^d$ may be each independently $C_1$-$C_{10}$ alkyl, wherein the alkyl or aryl in R may be further substituted with at least one selected from $C_1$-$C_{20}$ alkyl.

Preferably, in Formula 5 according to an embodiment of the present disclosure, R may be $C_1$-$C_{10}$ alkyl; $X^1$ and $X^2$ may be each independently halogen, $C_1$-$C_{10}$ alkyl, or acetylacetonate; A may be boron; $Y^1$ to $Y^4$ may be each independently fluorine-substituted $C_6$-$C_{12}$ aryl; $R^a$ to $R^d$ may be each independently $C_1$-$C_8$ alkyl, wherein the alkyl or aryl in R may be further substituted with at least one selected from $C_1$-$C_8$ alkyl. More preferably, $R^a$ to $R^d$ may be the same and may be $C_1$-$C_8$ alkyl.

Preferably, in the chromium complex of Formula 5 according to one embodiment of the present disclosure, R may be $C_1$-$C_5$ alkyl, and $R^a$ to $R^d$ may be $C_5$-$C_8$ alkyl. More preferably, R may be branched $C_3$-$C_5$ alkyl, and $R^a$ to $R^d$ may be $C_5$-$C_8$ alkyl. Even more preferably, R may be an isopropyl group, $R^a$ to $R^d$ may be an octyl group (n-octyl), and $[A(Y^1)(Y^2)(Y^3)(Y^4)]^-$ may be $[B(C_6F_5)_4]^-$. The chromium complex having the structure exemplified above, when applied to a catalyst system for ethylene oligomerization reaction, can further reduce the production of polyethylene compounds as by-product while significantly improving activity and selectivity.

In the method for oligomerization of ethylene according to one embodiment of the present disclosure, the organic solvent is not particularly limited in the kind thereof, but may be a hydrocarbon solvent substituted or unsubstituted with halogen. Specifically, as the hydrocarbon solvent, an aliphatic hydrocarbon solvent having 4 to 20 carbon atoms, an aromatic hydrocarbon solvent having 6 to 20 carbon atoms, or a mixture thereof may be used. More specifically, examples of the hydrocarbon solvent substituted or unsubstituted with halogen include toluene, xylene, chlorobenzene, dichlorobenzene, dichloromethane, methylcyclohexene, cyclohexene, and the like. Preferably, the hydrocarbon solvent may be dichloromethane, methylcyclohexene, or cyclohexene. When the solvent exemplified above is used, polymerization activity is high and it is easier to separate the products 1-hexene and 1-octene from the solvent after the oligomerization reaction.

The oligomer according to one embodiment of the present disclosure may have a polyethylene content of 0.3 wt % or less, preferably 0.2 wt % or less, more preferably less than 0.1 wt %.

The method for oligomerization of ethylene according to one embodiment of the present disclosure is capable of maintaining process stability by suppressing the production of polyethylene while exhibiting high activity and selectivity, by using a specific chromium complex, cocatalyst, and chain transfer agent.

The present disclosure will be described in more detail below by way of examples. However, these examples are for illustrative purposes only and the present disclosure is not limited to these examples.

Production Example 1

A chromium complex represented by Formula A below was produced according to the following method.

[Formula A]

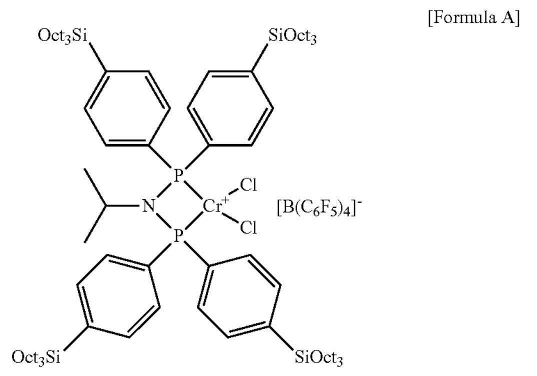

Synthesis of Cl—Si(n-Octyl)$_3$

A solution of acetyl chloride (1.54 g, 19.6 mmol) in $CH_2Cl_2$ (7 mL) was added dropwise to a $CH_2Cl_2$ (20 mL) solution containing trioctylsilane (4.83 g, 13.1 mmol) and $FeCl_3$ (0.0549 g, 0.262 mmol). After confirming that the color of the solution changed to yellow along with heat generation as $FeCl_3$ dissolved, the solution was stirred at room temperature for 24 hours. The solvent, the by-product acetaldehyde, and non-reactant acetyl chloride were removed through a vacuum line. The residue was dissolved in hexane (10 mL), and the insoluble brown solid ($FeCl_3$) was removed by Celite-aided filtration. The solvent was removed through a vacuum line to obtain the compound as a light yellow oil (4.98 g, 98%).

Synthesis of $BrC_6H_4$-p-Si(n-Octyl)$_3$ 1,4-dibromobenzene (3.31 g, 14.0 mmol) was dissolved in THF (35 mL), and n-butyllithium (5 mL, 2.5 M hexane solution, 12.5 mmol) was added thereto at −78° C., followed by stirring at −78° C. for 2 hours. A solution of Cl—Si(n-octyl)$_3$ (4.79 g, 11.9 mmol) in THF (6 mL) was added thereto, followed by reaction at room temperature for 3 hours. The solvent was removed through a vacuum line, the desired product was dissolved in hexane (18 mL), and then the insoluble white solid (LiBr) was removed by Celite-aided filtration. The solvent was removed from the filtered liquid by a vacuum line, and the residue was dissolved in hexane (18 mL) and passed through a short pad of silica gel (6.22 g). After removing the solvent through a vacuum line, the residue was vacuum-distilled at 80° C. to remove non-reactants (1,4-dibromobenzene), thus obtaining the desired compound as an oil (5.71 g, 92%).

Synthesis of ClP[$C_6H_4$-p-Si(n-Octyl)$_3$]$_2$ $BrC_6H_4$-p-Si(n-octyl)$_3$ (5.71 g, 10.9 mmol) was dissolved in THF (39 mL) and added to n-butyllithium (4.36 mL, 2.5 M hexane solution, 10.9 mmol) at −78° C., followed by stirring at −78° C. for 1 hour. Dichloro(diethylamino)phosphine (0.949 g, 5.45 mmol) dissolved in THF (9 mL) was added thereto over for 15 minutes, followed by reaction at 5° C. for 2 hours. After adding methylcyclohexane (19 mL) thereto, the solvent was removed through a vacuum line at room temperature, and the residue was added to methylcyclohexane (31 mL). Insoluble white solids (LiBr and LiCl) were removed by Celite-aided filtration. After removing the solvent, $PCl_3$ (4.12 g, 30.0 mmol) was added to the residue, followed by reaction at 70° C. for 2 hours. The non-reactant $PCl_3$ and the by-product dichloro(diethylamino)phosphine were removed by vacuum distillation at 80° C., thus obtaining an yellow oil compound. The oil compound was dissolved in hexane (23 mL), and insoluble by-products were removed by Celite-aided filtration. The solvent was removed through a vacuum line, thus obtaining the desired compound as a yellow oil (5.18 g, 99%).

Synthesis of i-PropylN[P($C_6H_4$-p-Si(n-Octyl)$_3$)$_2$]$_2$

A solution of i-PrNH$_2$ (0.135 g, 2.28 mmol) in $CH_2Cl_2$ (11 mL) was added dropwise to a $CH_2Cl_2$ (19 mL) solution containing ClP[$C_6H_4$-p-Si(n-octyl)$_3$]$_2$ (4.79 g, 5.02 mmol) and $Et_3N$ (2.31 g, 22.8 mmol). After the reaction solution was stirred at room temperature for 12 hours, volatile components were removed through a vacuum line. After adding hexane (40 mL) to the residue, the insoluble by-product $(Et_3NH)^+Cl^-$ was removed by Celite-aided filtration. The filtered liquid was passed through a short pad of silica gel pretreated with hexane/$Et_3N$ (v/v, 50:1), and then the solvent was removed through a vacuum line, thus obtaining the desired compound as a colorless oil (4.26 g, 98%).

Synthesis of [(i-PropylN[P($C_6H_4$-p-Si(n-Octyl)$_3$)$_2$]$_2$)—$CrCl_2$]$^+$[B($C_6F_5$)$_4$]$^-$ A solution of i-PropylN[P($C_6H_4$-p-Si(n-Octyl)$_3$)$_2$]$_2$ (1.41 g, 0.742 mmol) in $CH_2Cl_2$ (13 mL) was added dropwise to a solution of [$CrCl_2$($NCCH_3$)$_4$]$^+$[B($C_6F_5$)$_4$]$^-$ (0.715 g, 0.742 mmol) in $CH_2Cl_2$ (4.5 mL). After the reaction solution was stirred at room temperature for 2.5 hours, the solvent was removed through a vacuum line, thus obtaining a viscous green oil.

The obtained oil was dissolved in methylcyclohexane (5 mL), and then the solvent was removed through a vacuum line. This process was repeated until $CH_3CN$ and $CH_3Cl_2$ were completely removed, thus obtaining a viscous green oil (2 g, 100%). The obtained oil way was dissolved in methylcyclohexane (23.4 mL) to make a 10 wt % solution which was used for ethylene oligomerization.

[Example 1] Ethylene Oligomerization Reaction 200 ml of methylcyclohexane, 100 μmol of trinoctylaluminum (TnOA), and 200 μmol of diethylzinc (DEZ) were injected into a 500-ml autoclave reactor heated to 40° C., and then the chromium complex of Formula A (1.5 mg, 0.6 μmol) produced in Production Example 1 was injected into the reactor using a syringe. Then, ethylene gas was fed at a pressure of 500 psig. After the reaction was carried out at a temperature of 40° C. for 30 minutes while ethylene was continuously fed ethylene to maintain the internal pressure of the reactor at 500 psig, the reaction was terminated by cooling the reactor and discharging ethylene gas. For product analysis, the weight ratio of the product was calculated by measuring the contents of the produced oligomers {1-octene (1-C8), 1-hexene (1-C6), methylcyclopentane+methylenecyclopentane (cy-C6), and higher oligomers above C10 (>C10)} through gas chromatography (GC) analysis. The produced solid polyethylene was separated by filtration at room temperature and then the weight thereof was measured. The weight percent (wt %) of the polyethylene was calculated using the following equation: Weight (g) of produced PE/total weight (g) of product weight (g).

[Example 2] Ethylene Oligomerization Reaction

Ethylene oligomerization reaction was performed in the same manner as in Example 1, except that 400 μmol of diethylzinc (DEZ) was used.

[Example 3] Ethylene Oligomerization Reaction

Ethylene oligomerization reaction was performed in the same manner as in Example 1, except that 600 μmol of diethylzinc (DEZ) was used.

[Comparative Example 1] Ethylene Oligomerization Reaction

Ethylene oligomerization reaction was performed in the same manner as Example 1, except that diethylzinc (DEZ) was not injected.

Table 1 below shows the activities of the olefin polymerization reactions of Examples 1 to 3 and Comparative Example 1 and the compositions of the produced polymers.

TABLE 1

| | Amount (μmol) of diethylzinc injected | Activity (kg/g-Cr/hr) | 1-C8 (wt %) | 1-C6 (wt %) | Cy-C6 (wt %) | C10+ (wt %) | PE (wt %) |
|---|---|---|---|---|---|---|---|
| Example 1 | 200 | 5,770 | 75.8 | 9.8 | 5.2 | 9.1 | 0.06 |
| Example 2 | 400 | 6,561 | 74.3 | 10.9 | 5.3 | 9.4 | 0.02 |
| Example 3 | 600 | 5,467 | 74.2 | 10.9 | 5.4 | 9.4 | 0.02 |
| Comparative Example 1 | 0 | 5,066 | 75.8 | 9.7 | 5.1 | 8.4 | 1.03 |

Figure 2:
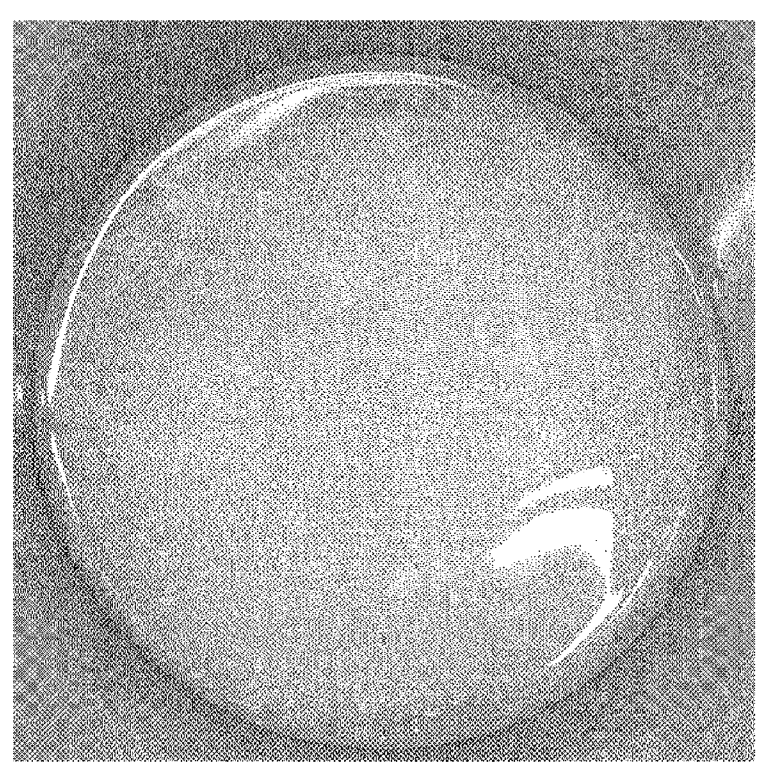
FIG. 2 is a photograph of the polymer produced after the reaction in Comparative Example 1 of the present disclosure.

As shown in Table 1, it can be confirmed that, in the case of Examples 1 to 3 in which DEZ was injected, the activity was better than that in Comparative Example 1 in which DEZ was not injected, and the amount of polyethylene produced was reduced by 90% or more. Referring to FIGS. 1 and 2, the difference in polyethylene that accumulated in the reactors after completion of the reaction can be clearly seen. The method for oligomerization of ethylene according to one embodiment of the present disclosure is capable of producing ethylene oligomers with excellent selectivity and conversion through high catalytic activity by performing the oligomerization reaction using a specific catalyst and cocatalyst at a controlled temperature. Moreover, the method for oligomerization of ethylene is capable of mass production by performing ethylene oligomerization even at low temperatures. Thus, the method is very advantageous for commercialization.

In addition, the method for oligomerization of ethylene according to one embodiment of the present disclosure is it very economical because it is capable of maintaining process stability by significantly reducing the production of polyethylene that causes tube clogging and fouling.

In addition, the method for oligomerization of ethylene according to one embodiment of the present disclosure is very economical because it uses the chromium complex represented by Formula 1 without using conventional expensive methylaluminoxane. Also, the method exhibits excellent catalytic activity, making ethylene oligomerization possible even at low temperatures, and thus may be applied to various reactors.

The above description of the present disclosure is exemplary, and those of ordinary skill in the art will appreciate that various modifications and variations are possible without departing from the technical spirit or essential characteristics of the present disclosure. In addition, the present embodiments are provided for illustrative purposes only but not intended to limit the technical concept of the present disclosure, and the scope of the technical concept of the present disclosure is not limited by these embodiments. The scope of protection of the present disclosure should be interpreted in accordance with the appended claims, and all technical ideas within the scope equivalent thereto should be interpreted as being included in the scope of rights of the present disclosure.

INDUSTRIAL APPLICABILITY

The method for oligomerization of ethylene according to one embodiment of the present disclosure may not only produce 1-hexene and 1-octene with high selectivity without reducing catalyst activity, but also significantly reduce the production of polyethylene that impairs process stability.

The invention claimed is:

1. A method for oligomerization of ethylene, comprising a step of producing an ethylene oligomer by reacting ethylene with a catalyst, a cocatalyst, and a chain transfer agent in the presence of an organic compound, wherein the ethylene oligomer contains an amount of polyethylene that is 0.1 wt % or less; and wherein the catalyst is a chromium complex represented by Formula 1 below, the cocatalyst is an organoaluminum compound represented by Formula 2 below, and the chain transfer agent is a compound represented by Formula 3 below:

[Formula 1]

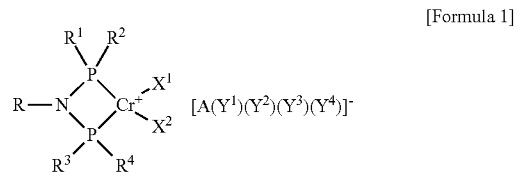

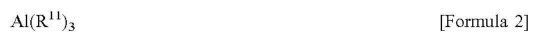

[Formula 2]

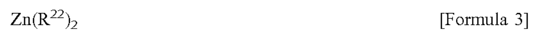

[Formula 3]

wherein

R is a $C_1$-$C_{60}$ alkyl, a $C_6$-$C_{60}$ aryl, or a $C_2$-$C_{60}$ heteroaryl containing at least one heteroatom selected from the group consisting of O, N, S, Si and P;

$R^1$ to $R^4$ are each independently $C_1$-$C_{60}$ alkyl, $C_6$-$C_{60}$ aryl, or $C_2$-$C_{60}$ heteroaryl containing at least one heteroatom selected from the group consisting of O, N, S, Si and P;

$X^1$ and $X^2$ are each independently halogen, $C_1$-$C_{30}$ alkyl, $C_1$-$C_{30}$ alkylcarboxylate, acetylacetonate, or $C_1$-$C_{30}$ hydrocarbyl containing at least one selected from among ether and amino;

A is boron or aluminum;

$Y^1$ to $Y^4$ are each independently fluorine-substituted $C_6$-$C_{60}$ aryl, fluorine-substituted $C_6$-$C_{60}$ heteroaryl containing at least one heteroatom selected from the group consisting of O, N, S, Si and P, fluorine-substituted $C_6$-$C_{60}$ aryloxy, or fluorine-substituted $C_6$-$C_{60}$ alkoxy;

$R^{11}$ is $C_4$-$C_8$ alkyl; and $R^{22}$ is $C_1$-$C_8$ alkyl, wherein the alkyl, aryl or heteroaryl in R, $R^1$ to $R^4$, $X^1$, $X^2$, $Y^1$ to $Y^4$, $R^{11}$, and $R^{22}$ are optionally further substituted with at least one selected from among $C_1$-$C_{30}$ alkyl, $C_6$-$C_{30}$ aryl, $C_1$-$C_{30}$ alkoxy, mono($C_1$-$C_{30}$)alkylamino, di($C_1$-$C_{30}$)alkylamino, tri($C_1$-$C_{30}$)alkylamino, mono($C_6$-$C_{30}$)arylamino, di($C_6$-$C_{30}$)arylamino, tri($C_6$-$C_{30}$)arylamino, mono($C_1$-$C_{30}$)alkylsilyl, di($C_1$-$C_{30}$)alkylsilyl, tri($C_1$-$C_{30}$)alkylsilyl, mono($C_6$-$C_{30}$)arylsilyl, di($C_6$-$C_{30}$)arylsilyl, and tri($C_6$-$C_{30}$)arylsilyl.

2. The method of claim 1, wherein $R^{11}$ in Formula 2 is an n-octyl group.

3. The method of claim 1, wherein $R^{22}$ in Formula 3 is ethyl.

4. The method of claim 1, wherein the reaction is performed at higher than 30° C. to lower than 60° C. for 10 minutes to 2 hours.

5. The method of claim 1, wherein a molar ratio between the chromium complex and the organoaluminum compound is 1:10 to 300.

6. The method of claim 1, wherein a molar ratio between the chromium complex and the organozinc compound is 1:100 to 700.

7. The method of claim 1, wherein Formula 1 is represented by Formula 4 below:

[Formula 4]

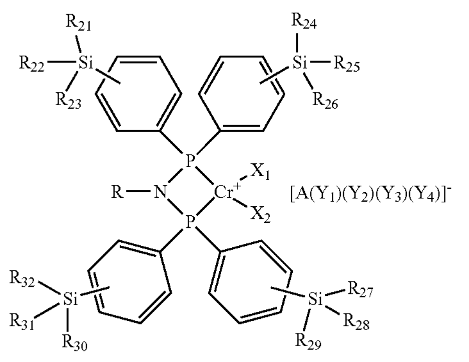

wherein $R^{21}$ to $R^{32}$ are each independently $C_1$-$C_{20}$ alkyl.

8. The method of claim 7, wherein Formula 1 is represented by Formula 5 below:

[Formula 5]

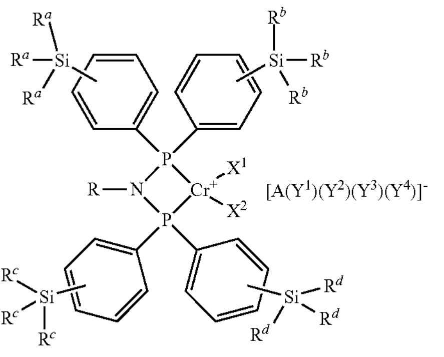

wherein $R^a$ to $R^d$ are each independently $C_1$-$C_{10}$ alkyl.

9. The method of claim 1, wherein R is a $C_2$-$C_{60}$ heteroaryl containing at least one heteroatom selected from the group consisting of O, N, S, Si and P.

10. The method of claim 1, wherein the step of producing the ethylene oligomer comprises reacting the catalyst and the co-catalyst to form a mixture, and then sequentially adding the chain transfer agent and the ethylene to the mixture.

11. An ethylene oligomer produced by reacting ethylene with a catalyst, a cocatalyst, and a chain transfer agent, wherein the ethylene oligomer contains an amount of polyethylene that is 0.1 wt % or less; and wherein the catalyst is a chromium complex represented by Formula 1 below, the cocatalyst is an organoaluminum compound represented by Formula 2 below, and the chain transfer agent is a compound represented by Formula 3 below:

[Formula 1]

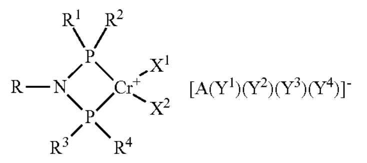

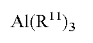

[Formula 2]

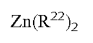

[Formula 3]

wherein

R is a $C_1$-$C_{60}$ alkyl, a $C_6$-$C_{60}$ aryl, or $C_2$-$C_{60}$ heteroaryl containing at least one heteroatom selected from the group consisting of O, N, S, Si and P;

$R^1$ to $R^4$ are each independently $C_1$-$C_{60}$ alkyl, $C_6$-$C_{60}$ aryl, or $C_2$-$C_{60}$ heteroaryl containing at least one heteroatom selected from the group consisting of O, N, S, Si and P;

$X^1$ and $X^2$ are each independently halogen, $C_1$-$C_{30}$ alkyl, $C_1$-$C_{30}$ alkylcarboxylate, acetylacetonate, or $C_1$-$C_{30}$ hydrocarbyl containing at least one selected from among ether and amino;

A is boron or aluminum;

$Y^1$ to $Y^4$ are each independently fluorine-substituted $C_6$-$C_{60}$ aryl, fluorine-substituted $C_6$-$C_{60}$ heteroaryl containing at least one heteroatom selected from the group consisting of O, N, S, Si and P, fluorine-substituted $C_6$-$C_{60}$ aryloxy, or fluorine-substituted $C_6$-$C_{60}$ alkoxy;

$R^{11}$ is $C_4$-$C_8$ alkyl; and $R^{22}$ is $C_1$-$C_8$ alkyl, wherein the alkyl, aryl or heteroaryl in R, $R^1$ to $R^4$, $X^1$, $X^2$, $Y^1$ to $Y^4$, $R^{11}$, and $R^{22}$ are optionally further substituted with at least one selected from among $C_1$-$C_{30}$ alkyl, $C_6$-$C_{30}$ aryl, $C_1$-$C_{30}$ alkoxy, mono($C_1$-$C_{30}$)alkylamino, di($C_1$-$C_{30}$)alkylamino, tri($C_1$-$C_{30}$) alkylamino, mono($C_6$-$C_{30}$) arylamino, di($C_6$-$C_{30}$) arylamino, tri($C_6$-$C_{30}$) arylamino, mono($C_1$-$C_{30}$)alkylsilyl, di($C_1$-$C_{30}$)alkylsilyl, tri($C_1$-$C_{30}$)alkylsilyl, mono($C_6$-$C_{30}$) arylsilyl, di($C_6$-$C_{30}$) arylsilyl, and tri ($C_6$-$C_{30}$) arylsilyl.

12. The ethylene oligomer of claim 11, wherein $R^{11}$ in Formula 2 is an n-octyl group.

13. The ethylene oligomer of claim 11, wherein $R^{22}$ in Formula 3 is ethyl.

14. The ethylene oligomer of claim 11, wherein the reaction is performed at higher than 30° C. to lower than 60° C. for 10 minutes to 2 hours.

15. The ethylene oligomer of claim 11, wherein a molar ratio between the chromium complex and the organoaluminum compound is 1:10 to 300.

16. The ethylene oligomer of claim 11, wherein a molar ratio between the chromium complex and the organozinc compound is 1:100 to 700.

17. The ethylene oligomer of claim 11, wherein Formula 1 is represented by Formula 4 below:

[Formula 4]

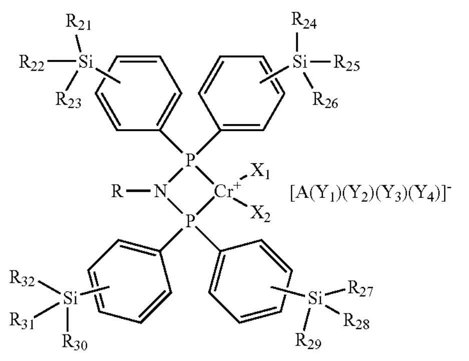

wherein $R^{21}$ to $R^{32}$ are each independently $C_1$-$C_{20}$ alkyl.

18. The ethylene oligomer of claim 11, wherein Formula 1 is represented by Formula 5 below:

[Formula 5]

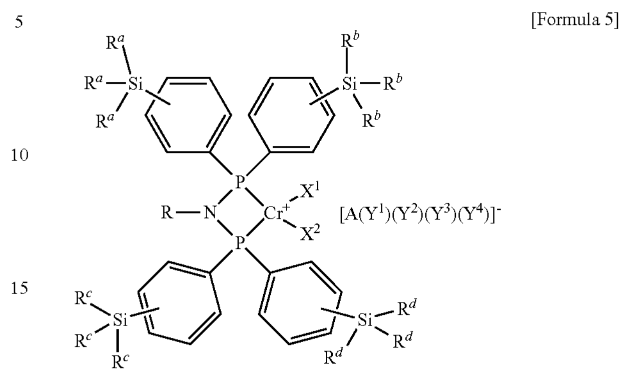

wherein $R^a$ to $R^d$ are each independently $C_1$-$C_{10}$ alkyl.

19. The ethylene oligomer of claim 11, wherein R is a $C_2$-$C_{60}$ heteroaryl containing at least one heteroatom selected from the group consisting of O, N, S, Si and P.

20. The ethylene oligomer of claim 11, wherein the ethylene oligomer is produced by reacting the catalyst and the co-catalyst to form a mixture, and then sequentially adding the chain transfer agent and the ethylene to the mixture.

* * * * *